US005837249A

United States Patent [19]

Heber-Katz et al.

[11] Patent Number: 5,837,249

[45] Date of Patent: Nov. 17, 1998

[54] METHOD FOR GENERATING AN IMMUNOGENIC T CELL RESPONSE PROTECTIVE AGAINST A VIRUS

[75] Inventors: Ellen Heber-Katz, Philadelphia; Bernhard Dietzschold, Newtown Square, both of Pa.

[73] Assignee: The Wistar Institute, Philadelphia, Pa.

[21] Appl. No.: 139,609

[22] Filed: Oct. 20, 1993

Related U.S. Application Data

[63] Continuation of Ser. No. 868,946, Apr. 15, 1992, abandoned, which is a continuation-in-part of Ser. No. 685,459, Apr. 12, 1991, abandoned, which is a continuation of Ser. No. 47,443, May 8, 1987, abandoned, which is a continuation-in-part of Ser. No. 725,087, Apr. 19, 1985, abandoned.

[51] Int. Cl.[6] ........................ A61K 39/12; A61K 39/205; A61K 39/245; C07K 14/145

[52] U.S. Cl. .................................... 424/186.1; 424/185.1; 424/196.11; 424/229.1; 424/231.1; 424/224.1; 530/323; 530/326

[58] Field of Search ............................ 424/88, 89, 185.1, 424/186.1, 196.11, 229.1, 231.1, 224.1; 530/323, 328, 395, 824, 825, 826, 326

[56] References Cited

U.S. PATENT DOCUMENTS

| | | | |
|---|---|---|---|
| 4,474,757 | 10/1984 | Arnon et al. | 424/88 |
| 4,565,696 | 1/1986 | Heath et al. | 424/88 |
| 4,709,011 | 11/1987 | Cohen et al. | 530/324 |
| 4,847,080 | 7/1989 | Neurath et al. | 424/89 |
| 5,019,383 | 5/1991 | Hopp | 424/88 |

FOREIGN PATENT DOCUMENTS

| | | |
|---|---|---|
| 1265054 | 1/1990 | Canada . |
| 093851 | 3/1982 | European Pat. Off. . |
| 203676 | 12/1986 | European Pat. Off. . |
| 237686 | 9/1987 | European Pat. Off. . |
| 290246 | 11/1988 | European Pat. Off. . |
| 8300182 | 9/1983 | WIPO . |

OTHER PUBLICATIONS

Allan, JS, "Human Immunodeficiency Virus–Related Infections in Animal Model Systems," in *AIDS: Biology, Diagnosis,Treatment and Prevention* (4th Ed.) (Ed. DeVita, Jr. et al., Lippincott–Raven Publishers) pp. 15–27 (1997).

Hackett et al.,"Stimulation of cytotoxic T cells by liposomes containing influenze virus or its components," Immunology (1983 Jun.) 49 (2) 255–63.

Lawman et al., "Cell — mediated immunity to herpes simplex virus: induction of cytotoxic T lymphocyte responses by viral antigens incorporated into liposomes," Journal of Immunology (1981 Jan.) 126 (1) 304–8.

Clerici, et al., "The Th1–Th2 Hypothesis of HIV Infection: New Sights," *Immunology Today,* vol. 15, No. 12, pp. 575–581, (1994).

Coon, et al., "Selective Induction of Delayed Hypersensitivity by a Lipid Conjugated Protein Antigen Which is Localized in Thymus Dependent Lymphoid Tissue," *Journal of Immunology,* vol. 110, No. 1, pp. 183–190 (1973).

Milich, David R. "Probing T Cell Antigen Recognition: Use of Synthetic Peptides" *Peptide Research,* vol. 3, No. 2, pp. 85–96, (1990).

Ertl et al. (1989) J. Virol. 63 : 2885–2892.

Hopp et al., Mol. Immunol. 21:13–16 (1984) [Hopp I].

Merrifield, J. Amer. Chem. Soc. 65:2149–2152 (1963).

Eisenberg et al, J. Virol. 53:634–644 (1985) [Eisenberg I].

Cohen et al, J. Virol. 49:102–108 (1984) [Cohen I].

Thibodeau et al, Genetic Variations Among Influenze Viruses, Academic Press, Inc., New York (1981), pp. 587–600.

Arnnon et al, J. Immunol. Meth. 61:261–273 (1983).

Hopp et al, Proc. Nat'l. Acad. Sci. USA 78:3824–3828 (1981) [Hopp II].

Wilson et al, Cell 37:767–778 (1984).

Lerner, Sci. American pp. 66–74 (1983).

Dietzschold et al, J. Virol. 52:531–435 (1984).

Eisenberg et al, J. Virol 49:265–268 (1984) [Eisenberg II].

Rawls et al, J. Virol. 51:263–265 (1984).

Seid et al, J. Biol. Chem. 256:7305–7310 (1981).

Hopp et al, Chem. Abstracts 156990s, vol. 100 (1984) [Hopp III].

Berman et al, Chem. Abstracts 164960p, vol. 102 (1985).

Watson et al, Chem. Abstracts 180101y, vol. 100 (1984).

Cohen et al, Chem. Abstracts 1977772r, vol. 100 (1984) [Cohen II].

Watari et al, J. Exp. Med. 165:459–470 (1987).

Heber–Katz et al, Current Topic Microbiol. Immunol. 130:51 (1986).

Long et al, Infect. Immun. 37:761–764 (1984).

Blalanchandran et al, Infect. Immun. 37:1132–1137 (1982).

Dix et al, Infect. Immun. 34:192–199 (1981).

Kapoor et al, J. Gen. Virol. 60:225–233 (1982).

Wilson, et al, J. Immunology 132:1522–1528 (1984).

Babiuk et al, J. Mircobiology 25:267 (1979).

Townsen et al, Cell 44:959–968 (1986).

Puddington et al, J. Virol. 60:708–717 (1986).

Celis et al, J. Immunol. 136:692–697 (1986).

Hattwick et al, The Natural History of Rabies (Baer, G., ed.) 2:282–301 (1975).

(List continued on next page.)

*Primary Examiner*—Michael P. Woodward
*Attorney, Agent, or Firm*—Banner & Witcoff, Ltd.

[57] ABSTRACT

A novel method of presenting an immunogenic peptide to an antigen presenting cell (APC) of a mammalian host, in order to generate a T cell response protective against a virus, such as herpes or rabies virus, comprising administering an immunologically effective amount of (1) a peptide-fatty acid conjugate, the peptide having the amino acid sequence corresponding to the sequence of a fragment of a glycoprotein or protein of the virus which produces a T cell response or a synthetic replica thereof, (2) a liposome composition and (3) an adjuvant so that the peptide protrudes from the liposome and when the liposome fuses with the APC, the peptide remains bound to the cell surface of the APC membrane.

21 Claims, 6 Drawing Sheets

OTHER PUBLICATIONS

Wiktor et al, Proc. Natl. Acad. Sci. USA 75:3938–3942 (1978) [Wiktor I].
Wiktor et al, J. Exp. Med. 152:99–112 (1980) [Wiktor II].
Rupprecht et al, Proc. Natl. Acad. Sci. USA 83:7947–7950 (1986).
Wiktor et al, Proc. Natl. Acad. Sci. USA 74:334–338 (1977) [Wiktor III].
Turner, Arch. Virol. 61:321–325 (1979).
Smith, Infect. Immun. 31:297–308 (1981).
Wiktor et al, Rabies in the Tropics, Kuwert et al, eds, pp. 21–29 Springer–Verlag, Berlin (1985).
Turner, Ann. Virol. (Inst. Pasteur) 136E:453–460 (1985).
Yewdell et al, J. Exp. Med. 163:1529–1538 (1986).
Sokol et al, J. Virol. 7:241–249 (1971).
Dietzschold et al, Virology, 98:63–75 (1979) [Dietzschold II].
Schneider et al, J. Virol. 11:748–755 (1973).
Sokol et al, Proc. Natl. Acad. Sci. USA 72:933–936 (1975) [Sokol II].
Cox et al, The Replication of Negative Strand Viruses (Bishop, DHL and Compans, R.W., eds.) pp. 639–645 Elsevier/North–Holland, Inc. New York (1981).
Wunner et al, Immuno. of Viruses (van Regenmortel, MHV and Neurath, AR, eds) pp. 367–388 Elsevier Sci. Publ. BV, Amsterdam (1985).
Tignor et al, J. Gen. Virol. 37:595–611 (1977).
Lafon et al, J. Gen. Vir. 66:2125–2133 (1985).
Sokol et al, Virology, 52:246–263 (1973) [Sokol III].
Tordo et al, Nucleic Acids Res. 14:2671–2683 (1986).
N. Tordo et al, Proc. Natl. Acad. Sci. USA, 83:3914–3918 (1986) [Tordo II].
Wilson et al, J. Immunol., 132(3) :1522–1528 (1984).
Ho et al, Biochem., 25:5500–5506 (1986).
Van Regenmortel, TIBS, 11:36–39 (1986).
Shinnick et al, Ann. Rev. Microbiol., 37:425–446 (1983).
Hunsmann, Chem. Abstr., 98:345, abstr. 78117m (1983).
Visser et al, Chem Abstr., 103:59294x (1985) [Visser I].
Visser et al, Chem. Abstr., 103:59295y (1985) [Visser II].
Heber–Katz et al, J. Exp. Med., 167:275–287 (1988) [Heber–Katz II].
Dietzschold et al, Virus Res., 8:103–125 (1987) [Dietzschold III].
Watson, Gene, 26:307–312 (1983).
Dietzschold et al, Proc. Natl. Acad. Sci. USA, 84:9165–9169 (1987) [Dietzschol IV].
Heber–Katz et al, Processing and Presentation of Antigens, pp. 133–141 (1988) [Heber–Katz III].
M. J. Bevan, Nature, 342:479 (1989).
Deres et al, Nature, 342:561 (1989).

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 369 amino acids
( B ) TYPE: amino acid
( D ) TOPOLOGY: unknown ( i i ) MOLECULE TYPE: peptide ( x i ) SEQUENCE DESCRIPTION: SEQ ID NO:1:

```
Lys Tyr Ala Leu Ala Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

Gly Val Arg Arg Val Tyr His Ile Gln Ala Gly Leu Pro Asp Pro Phe
        35                  40                  45

Gln Pro Pro Ser Leu Pro Ile Thr Val Tyr Tyr Ala Val Leu Glu Arg
    50                  55                  60

Ala Cys Arg Ser Val Leu Leu Asn Ala Pro Ser Glu Ala Pro Gln Ile
65                  70                  75                  80

Val Arg Gly Ala Ser Glu Asp Val Arg Lys Gln Pro Tyr Asn Leu Thr
                85                  90                  95

Ile Ala Trp Phe Arg Met Gly Gly Asn Cys Ala Ile Pro Ile Thr Val
            100                 105                 110

Met Glu Tyr Thr Glu Cys Ser Tyr Asn Lys Ser Leu Gly Ala Cys Pro
        115                 120                 125

Ile Arg Thr Gln Pro Arg Trp Asn Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Lys Gly Ser Cys Lys Tyr Ala
            180                 185                 190

Leu Pro Leu Arg Ile Pro Pro Ser Ala Cys Leu Ser Pro Gln Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Val Tyr Ser Leu Lys Ile Ala Gly
225                 230                 235                 240

Trp His Gly Pro Lys Ala Pro Tyr Thr Ser Thr Leu Leu Pro Pro Glu
                245                 250                 255

Leu Ser Glu Thr Pro Asn Ala Thr Gln Pro Glu Leu Ala Pro Glu Asp
            260                 265                 270

Pro Glu Asp Ser Ala Leu Leu Glu Asp Pro Val Gly Thr Val Ala Pro
        275                 280                 285

Gln Ile Pro Pro Asn Trp His Ile Pro Ser Ile Gln Asp Ala Ala Thr
    290                 295                 300

Pro Tyr His Pro Pro Ala Thr Pro Asn Asn Met Gly Leu Ile Ala Gly
305                 310                 315                 320

Ala Val Gly Gly Ser Leu Leu Ala Ala Leu Val Ile Cys Gly Ile Val
```

-continued

```
                    325                          330                          335

Tyr Trp Met His Arg Arg Thr Arg Lys Ala Pro Lys Arg Ile Arg Leu
            340                     345                     350

Pro His Ile Arg Glu Asp Asp Gln Pro Ser Ser His Gln Pro Leu Phe
        355                     360                     365

Tyr
```

( 2 ) INFORMATION FOR SEQ ID NO:2:

( i ) SEQUENCE CHARACTERISTICS:
( A ) LENGTH: 16 amino acids
( B ) TYPE: amino acid
( D ) TOPOLOGY: unknown ( i i ) MOLECULE TYPE: peptide ( x i ) SEQUENCE DESCRIPTION: SEQ ID NO:2:

```
Ser Leu Lys Met Ala Asp Pro Asn Arg Phe Arg Gly Lys Asn Leu Pro
1               5                   10                  15
```

( 2 ) INFORMATION FOR SEQ ID NO:3:

( i ) SEQUENCE CHARACTERISTICS:
( A ) LENGTH: 25 amino acids
( B ) TYPE: amino acid
( D ) TOPOLOGY: unknown ( i i ) MOLECULE TYPE: peptide ( x i ) SEQUENCE DESCRIPTION: SEQ ID NO:3:

```
His Phe Val Gly Cys Tyr Met Gly Gln Val Arg Ser Leu Asn Ala Thr
1               5                   10                  15

Val Ile Ala Ala Cys Ala Pro His Glu
            20                  25
```

( 2 ) INFORMATION FOR SEQ ID NO:4:

( i ) SEQUENCE CHARACTERISTICS:
( A ) LENGTH: 23 amino acids
( B ) TYPE: amino acid
( D ) TOPOLOGY: unknown ( i i ) MOLECULE TYPE: peptide ( x i ) SEQUENCE DESCRIPTION: SEQ ID NO:4:

```
Lys Tyr Ala Leu Ala Asp Pro Ser Leu Lys Met Ala Asp Pro Asn Arg
1               5                   10                  15

Phe Arg Gly Lys Asn Leu Pro
            20
```

( 2 ) INFORMATION FOR SEQ ID NO:5:

( i ) SEQUENCE CHARACTERISTICS:
( A ) LENGTH: 25 amino acids
( B ) TYPE: amino acid
( D ) TOPOLOGY: unknown ( i i ) MOLECULE TYPE: peptide ( x i ) SEQUENCE DESCRIPTION: SEQ ID NO:5:

```
His Phe Val Gly Cys Tyr Met Gly Gln Val Arg Ser Leu Asn Ala Thr
1               5                   10                  15

Val Leu Ala Ala Cys Ala Pro His Glu
            20                  25
```

-continued ( 2 ) INFORMATION FOR SEQ ID NO:6:

( i ) SEQUENCE CHARACTERISTICS:
( A ) LENGTH: 16 amino acids
( B ) TYPE: amino acid
( D ) TOPOLOGY: unknown ( i i ) MOLECULE TYPE: peptide ( x i ) SEQUENCE DESCRIPTION: SEQ ID NO:6:

Ser Leu Lys Met Ala Asp Pro Asn Arg Phe Arg Gly Leu Asx Leu Pro
1 5 10 15

( 2 ) INFORMATION FOR SEQ ID NO:7:

( i ) SEQUENCE CHARACTERISTICS:
( A ) LENGTH: 23 amino acids
( B ) TYPE: amino acid
( D ) TOPOLOGY: unknown ( i i ) MOLECULE TYPE: peptide ( i x ) FEATURE:
( A ) NAME/KEY: Peptide
( B ) LOCATION: 6..8
( D ) OTHER INFORMATION: /note= "Amino acid in position 7 can be either pro or ala."

( x i ) SEQUENCE DESCRIPTION: SEQ ID NO:7:

Lys Tyr Ala Leu Ala Asp Xaa Ser Leu Lys Met Ala Asp Pro Asn Arg
1 5 10 15

Phe Arg Gly Lys Asx Leu Pro
20

( 2 ) INFORMATION FOR SEQ ID NO:8:

( i ) SEQUENCE CHARACTERISTICS:
( A ) LENGTH: 10 amino acids
( B ) TYPE: amino acid
( D ) TOPOLOGY: unknown ( i i ) MOLECULE TYPE: peptide ( x i ) SEQUENCE DESCRIPTION: SEQ ID NO:8:

Asp Asp Gly Thr Val Asn Ser Asp Asp Glu
1 5 10

( 2 ) INFORMATION FOR SEQ ID NO:9:

( i ) SEQUENCE CHARACTERISTICS:
( A ) LENGTH: 19 amino acids
( B ) TYPE: amino acid
( D ) TOPOLOGY: unknown ( i i ) MOLECULE TYPE: peptide ( x i ) SEQUENCE DESCRIPTION: SEQ ID NO:9:

Leu Thr Lys Thr Asp Val Ala Leu Ala Asp Asp Gly Thr Val Asn Ser
1 5 10 15

Asp Asp Glu ( 2 ) INFORMATION FOR SEQ ID NO:10:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide -continued ( x i ) SEQUENCE DESCRIPTION: SEQ ID NO:10:

Tyr Glu Ala Ala Glu Leu Thr Lys Ser Asp Val Ala Leu Ala Asp
1 5 10 15

( 2 ) INFORMATION FOR SEQ ID NO:11:

( i ) SEQUENCE CHARACTERISTICS:
( A ) LENGTH: 20 amino acids
( B ) TYPE: amino acid
( D ) TOPOLOGY: unknown ( i i ) MOLECULE TYPE: peptide ( x i ) SEQUENCE DESCRIPTION: SEQ ID NO:11:

His His Thr Leu Met Thr Thr His Lys Met Cys Ala Asn Trp Ser Thr
1 5 10 15

Ile Pro Asn Pro
20

( 2 ) INFORMATION FOR SEQ ID NO:12:

( i ) SEQUENCE CHARACTERISTICS:
( A ) LENGTH: 26 amino acids
( B ) TYPE: amino acid
( D ) TOPOLOGY: unknown ( i i ) MOLECULE TYPE: peptide ( x i ) SEQUENCE DESCRIPTION: SEQ ID NO:12:

His Phe Val Gly Cys Tyr Met Gly Gln Val Arg Ser Leu Ala Asn Ala
1 5 10 15

Thr Val Ile Ala Ala Cys Ala Pro His Glu
20 25

( 2 ) INFORMATION FOR SEQ ID NO:13:

( i ) SEQUENCE CHARACTERISTICS:
( A ) LENGTH: 15 amino acids
( B ) TYPE: amino acid
( D ) TOPOLOGY: unknown ( i i ) MOLECULE TYPE: peptide ( x i ) SEQUENCE DESCRIPTION: SEQ ID NO:13:

Gly Lys Tyr Arg Glu Asp Phe Gln Met Asp Glu Gly Asp Pro Ser
1 5 10 15

METHOD FOR GENERATING AN IMMUNOGENIC T CELL RESPONSE PROTECTIVE AGAINST A VIRUS

This is a continuation of Ser. No. 868,946 filed Apr. 15, 1992, abandoned, which is a continuation-in-part of application Ser. No. 07/685,459, filed on Apr. 12, 1991, now abandoned which is a continuation of application Ser. No. 07/047,443, filed on May 8, 1987 now abandoned which is a continuation-in-part of application Ser. No. 06/725,087, filed on Apr. 19, 1985, now abandoned.

FIELD OF THE INVENTION

This invention relates to the methods of preparation and use of a vaccine capable of generating an immunogenic T cell response protective against a virus in the absence of antibody. Although illustrative embodiments of the invention described employ vaccines which provide significant protection for an extended period of time against a large dose of herpes virus or rabies virus, it is to be understood that, according to the invention, the methods of this invention may employ vaccines which offer protection against other viruses, such as, influenza, HTLV-III (AIDS), retroviruses and oncogenic viruses.

BACKGROUND OF THE INVENTION

In published protocols for immunization against viral infections, such as Herpes Simplex virus (HSV) and others, high antibody titers have been reported, leading to the conclusion that high antibody titers are extremely important in providing protection. However, as one illustration, recurrent herpes infections are observed often in the presence of high antibody levels in the serum of patients. Individuals who have been infected previously with HSV-1 and are synthesizing antibody which crossreacts with both HSV-1 and HSV-2, nevertheless, contract HSV-2 and have recurrent outbreaks of HSV-1 lesions. Perhaps more significantly, published studies have shown not only that antibody is unable to protect, but that antibody production can actually interfere with a protective host immune response [Wilson et al, *J. Immunology*, 132:1552–1528 (1984); Babiuk et al, *J. Microbiology*, 25:267 (1979)].

Townsend et al, *Cell*, 144:959–968 (1986); Puddington et al, *J. Virol.*, 60:708–717 (1986); and Celis et al, *J. Immunol.*, 136:692–697 (1986) have focused on the effect of internal viral antigens, as well as surface glycoproteins, upon viral infection and immunization, particularly the priming of regulatory and cytotoxic T lymphocytes (CTLs).

There is experimental data which indicates that immunization with whole herpes virus or with surface components of the virus can be protective. One such component is the 59,000 MW virus envelope glycoprotein D molecule (gD) [Long et al, *Infect. and Immunity*, 37:761–764 (1984)]. It has also been demonstrated that antibody to this molecule can neutralize the virus and thus, when passively injected into animals, may be protective [Blalanchandran et al, *Infect. and Immunity*, 37:1132–1137 (1982); Dix et al, *Infect and Immunity*, 34:192–199 (1981); Kapoor et al, *J. Gen. Virol.*, 60:225–233 (1982)].

Recognition of internal rabies viral proteins, in contrast to rabies surface glycoproteins, may not depend solely on the levels of virus-neutralizing antibodies induced by glycoprotein [Hattwick et al, The Natural History of Rabies (Baer, G., ed.) Vol. 2, pp. 282–301, Academic Press, New York, London (1975); Wiktor et al, *Proc. Natl. Acad. Sci. USA*, 75:3938–3942 (1978); Wiktor et al, *J. Exp. Med.*, 152:99–112 (1980); Rupprecht et al, *Proc. Natl. Acad. Sci. USA*, 83:7947–7950 (1986)]. The presence of virus-induced CTL during rabies infection or following immunization with live or inactivated rabies virus suggests a possible role for CTL in cell-mediated immunity [(Wiktor et al, *Proc. Natl. Acad. Sci. USA*, 74:334–338 (1977); Turner, *Arch. Virol.*, 61:321–325 (1979); Smith, *Infect. Immun.*, 31:297–308 (1981)] and a correlation between CTL involvement and protection [Wiktor et al, Rabies in the Tropics (Kuwert et al, eds.), pp. 21–29, Springer-Verlag, Berlin (1985); Turner, *Ann. Virol.* (*Inst. Pasteur*), 136E:453–460 (1985)].

The viral nucleocapsid protein of Vesicular Stomatitis Virus (VSV), which like rabies is within the rhabdovirus family, has been demonstrated to be the predominant cross-reactive antigen recognized by primary anti-VSV CTLs and is a major target antigen for secondary stimulation of anti-VSV CTLs [Puddington et al, (1986) supra.]. Epitopes on the nucleocapsid protein are major determinants of the killing effect of anti-viral CTLs [Yewdell et al, *J. Exp. Med.*, 163:1529–1538 (1986)].

The nucleoprotein (N protein) and the nominal phosphoprotein (NS protein), both of which are phosphorylated in rabies virus [Sokol et al, *J. Virol.*, 7:241–249 (1971); Dietzschold et al, *Virology*, 98:63–75 (1979)], represent major antigens in the internal nucleocapsid (NC) complex of rabies virus [Schneider et al, *J. Virol.*, 11:748–755 (1973); Sokol et al, *Proc. Natl. Acad. Sci. USA*, 72:933–936 (1975); Cox et al, The Replication of Negative Strand Viruses (Bishop, D.H.L. and Compans, R.W., eds.), pp. 639–645, Elsevier/North-Holland, Inc., New York (1981); Wunner et al, Immunochemistry of Viruses, The Basis for Seriodiagnosis and Vaccines (van Regenmortel, M.H.V. and Neurath, A.R., eds.), pp. 367–388, Elsevier Science Publishers B.V., Amsterdam (1985)]. For some time, it has been recognized that the NC proteins of all rabies viruses share common antigenic determinants.

Dietzschold et al, *Virus Res.*, 8: 103–145 (1987) is incorporated herein by reference for information on the N and NS rabies virus proteins, and protein fragments thereof useful in the present invention. This document describes the use of protein fragments and synthetic peptides to map antigenic domains of the ERA strain N and NS proteins within their deduced amino acid sequences and to locate the phosphorylation site of the N protein within its primary sequence. Also described is the structure of two antigenic sites of the N protein and one antigenic site of the NS protein. Synthetic peptides corresponding to the three antigenic regions of the N and NS proteins also stimulated proliferation of human T lymphocytes derived from vaccinees who received inactivated rabies virus vaccine. These results suggest that the antigenic regions of N and NS proteins are recognized by both B and T cells.

Viral peptides of various sources have been employed in numerous vaccine compositions in attempts to elicit protection against infection by a selected virus. See, for example, Cohen et al, U.S. Pat. No. 4,709,011; Hopp, European Patent Application No. 93,851 and Thibodeau et al, “Genetic Variations Among Influenza Viruses”, (1981). For example, according to the method of Cohen, an immunogenic Herpes Simplex virus peptide is presented to the antigen presenting cell (APC) in a haphazard manner. In practice, the immunogen becomes degraded and fails to elicit a cellular response.

In Hopp, a peptide-fatty acid composite used to immunize a host becomes encapsulated within the APC as micelles. Such micelles are endocytosed by the APC and dissolve in the acidic cell.

The method presented in Thibodeau results in entrapment of the peptides within a membrane so that upon fusion of the liposome with an APC, the contents are spilled into the cell, whereupon they become degraded.

What is needed in the art is a method of preparation and use of a vaccine that offers significant protection for a long period of time against a large scale viral infection, for example, by a herpes virus or rabies virus. This protection should be achieved by a limited number of immunizations, in many instances a single immunization.

SUMMARY OF THE INVENTION

The present invention provides methods of preparing and using vaccines capable of generating a T cell response protective against a virus in the substantial absence of antibody. These methods and compositions permit the presentation of the selected peptide antigen to the antigen presenting cell (APC) of the selected host in a manner which elicits a T cell response. The vaccine compositions of the present invention comprise an immunologically effective amount of a peptide-fatty acid conjugate. The peptide used in the conjugate has an amino acid sequence corresponding to the sequence of a fragment of a glycoprotein or protein of a selected virus which produces a T cell response, or a synthetic replica of the glycoprotein or protein fragment. The conjugate has the formula

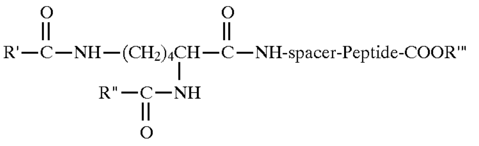

where R' and R" are alkyl groups containing from 5 to 30, preferably from 10 to 20 carbon atoms, and R'" is selected from the group consisting of hydrogen and at least one amino acid residue.

The vaccine compositions are prepared by combining the conjugate of the above formula with a liposome composition. The liposome is preferably a mixture of phosphatidyl choline, cholesterol and lysophosphatidyl choline. The compositions further include an adjuvant.

The resulting vaccine composition permits the peptide conjugate to protrude from the liposome, so that upon administration to the host, the peptide is membrane bound after fusion of the vaccine composition with the vaccinated host's antigen presenting cell.

As used in the specification and appended claims, the expression "T cell response" refers to the ability of T cells to respond to antigen by production of lymphokines and/or molecules involved in effector functions or cell-mediated effector functions on target cells.

Upon administration to the host the vaccine compositions of the present invention do not induce antibody, because of the results of the vaccine-APC fusion. Thus these compositions can avoid the phenomenon of "immune enhancement" in which antibodies enhance viral infectivity [Hawks et al, *J. Virol.*, 33:250 (1967); Halstead et al, *J. Immunol.*, 132:1526 (1984)]. This effect has been shown to be especially important in viruses that infect macrophages (i.e. HTLV-3).

An embodiment of the present invention is an anti-HSV-1 or HSV-2 vaccine composition in which the immunologically active peptide-fatty acid conjugate has an amino acid sequence corresponding to a fragment of herpes simplex virus type 1 envelope glycoprotein gD-1 or herpes simplex virus type 2 envelope glycoprotein gD-2, or a synthetic replica of such glycoprotein fragment. The fragment is capable of producing a T cell response and the conjugate is of the formula

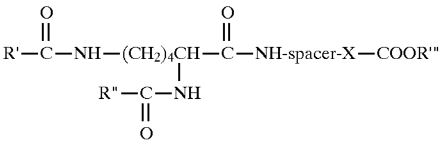

where R', R" and R'" are stated above, and X is an amino acid sequence corresponding to that of a fragment of herpes virus envelope glycoprotein. The N-terminal region of either gD-1 or gD-2 may comprise a synthetic peptide with sequence homology manually synthesized using Merrifield solid phase methods [Merrifield, *J. Am. Chem. Soc.*, 85:2194 (1963) and Merrifield, *Adv. Enzymol.*, 32:221–296 (1969)). The other components of the vaccine are as previously indicated. In a particularly preferred vaccine of the invention, X has the amino acid sequence [SEQ. ID. NO: 2]

-Ser-Leu-Lys-Met-Ala-Asp-Pro-Asn-Arg-Phe-Arg-Gly-Lys-Asn-Leu-Pro-;

R' and R" are alkyl groups containing 15 carbon atoms, R'" is a cysteine residue; and the adjuvant is alum.

Another vaccine is an anti-rabies vaccine in which the immunologically active peptide-fatty acid conjugate has an amino acid sequence corresponding to a synthetic peptide fragment, N-V12b, having the amino acid sequence [SEQ. ID. NO: 3]

$NH_2$—His—Phe—Val—Gly—Cys—Tyr—Met—Gly—

Glu—Val—Arg—Ser—Leu—Asn—Ala—Thr—Val—

Ile—Ala—Ala—Cys—Ala—Pro—His—Glu—, which corresponds to residues 279–291 of the rabies N protein [see, Dietzschold et al, *Virus Res.*, 8:103–125 (1987), incorporated by reference].

Such peptide-fatty acid conjugates may be prepared, for example, by adding a spacer, such as, Gly-Gly-Lys to the N-terminus of a viral glycoprotein which produces a T cell response, and then adding two fatty acid side chains to the amines of the N-terminal lysine. The coupling of the fatty acid moieties may be carried out by the symmetric anhydride method [Hopp, *Molecular Immunology*, 21:13–16 (1984)].

According to a preferred form of the invention, the Gly-Gly-Lys spacer is added to the N-terminal region of a fragment of the glycoprotein D molecule of HSV-1 or HSV-2 which produces a T cell response, following which a palmitic acid side chain is linked to each of the alpha and epsilon amino groups of the terminal lysine.

The resulting compositions of this invention are useful as anti-viral vaccines. Particularly anti-HSV-1 and anti-HSV-2 vaccines and anti-rabies vaccines are exemplified herein. However, other viral glycoproteins are expected to be useful in the methods of preparing and using vaccine compositions of the present invention, e.g., other members of the herpes virus group.

The methods and administration vaccines of the invention are capable of achieving significant protection against a large dose of virus with a single injection. This protection remains intact for a protracted period of time. Because prior researchers had concluded that high antibody titers were extremely important in providing protection against HSV-1 and HSV-2 infection, it is surprising that a protective immune response against HSV infection can be achieved without stimulating an antibody response. Rather, it has been discovered that with administration of a vaccine of this invention, a T cell proliferative response in the absence of an antibody response effectively confers long term protection.

DETAILED DESCRIPTION OF THE INVENTION

Figure 1:
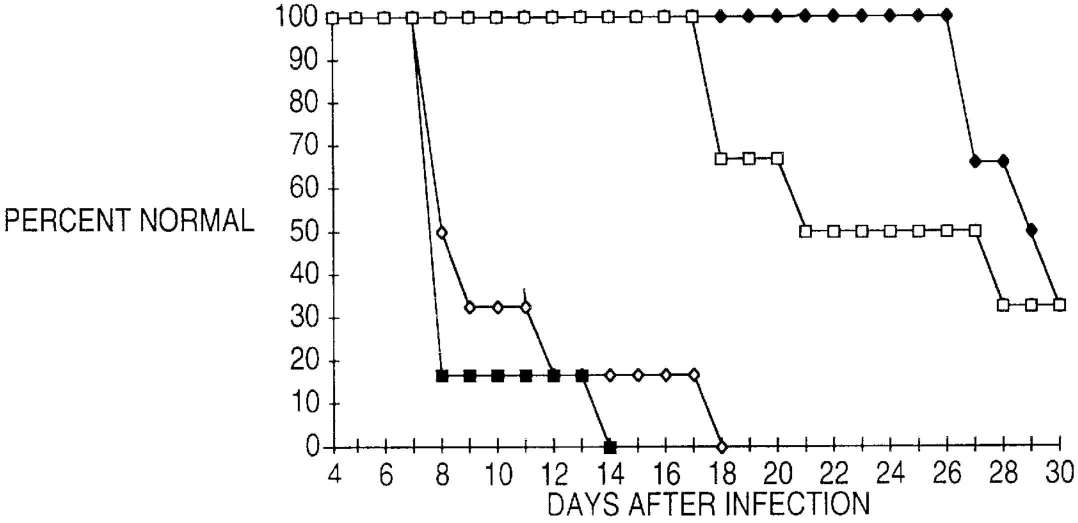
FIG. 1 is a plot of the percentage of normal mice vs. time (days) comparing the protection against lethal infection by HSV-2 provided by the vaccine of the present invention compared to certain control inoculants.

Stimulation of cellular immunity by an antigen is known to require association of an immunogen with an appropriate major histocompatibility complex (MHC) on an antigen presenting cell (APC). The present invention preferentially generates a cellular response by a novel method of presenting an immunogenic peptide to a host's APC. According to the present invention, after a selected viral peptide is prepared in a vaccine conjugate herein described, the vaccine conjugate, upon administration, is fused with the APC, and the peptide remains bound to the APC surface membrane. Thus, the peptide does not degrade within the cell. The proper association of the immunogenic peptide with the MHC on the cell surface confers T cell immunity, in preference to B cell or antibody immunity, in the host. Regardless of which immunogenic peptide is being presented to the APC, the inventors have observed a T-cell response to the immunogen. Several examples of this method and vaccine conjugates thereof are provided in this detailed description.

The present invention is directed to a method of inducing, in an animal, a T cell response to a selected peptide and to vaccine compositions for eliciting that response. The method of the present invention permits the vaccination of an animal with a peptide-fatty acid conjugate vaccine comprising a selected peptide or fragment of a peptide in association with a fatty acid, liposomes and an adjuvant, which vaccine is capable of eliciting a T cell response. The inventors have observed that a protective T cell response is elicited by this vaccine in the absence of detectable antibody.

It is this ability of the vaccination method, and indeed, the vaccine compositions themselves, to elicit primarily T cell protective immunity as well as the ability of the peptide to function with immunodominant and non-immunodominant peptides, which makes both the method and the vaccine compositions themselves, unique and valuable in the art.

Because the method and compositions elicit T cell protective response, such methods and compositions avoid undesirable immune enhancement. Immune enhancement is the participation of an antibody (B cell) response in a disease which has been found to detrimentally enhance the infection, rather than protect the vaccinee. The occurrence of the clinically adverse effects of antibody production has been observed in viruses like AIDS and HSV, among others.

It is not the particular antigen used in the method which confers patentability, but the method itself which permits appropriate presentation of an antigen to the cell.

The invention is described hereinafter by specific detailed reference to the preparation and testing for immunogenicity of illustrative anti-HSV-1 or HSV-2 vaccines and anti-rabies vaccines, each vaccine composition comprising a synthetic peptide-fatty acid conjugate. However, other viral peptides may also be employed in the method of this invention.

Considering the constituent parts of the vaccine, the HSV specific component of the peptide-fatty acid conjugate comprises a peptide having sequence homology with an N-terminal region or fragment of envelope glycoprotein D (gD) of either HSV-1 or HSV-2 which produces a T cell response or is recognized by a T cell.

The peptide may be the entire 23 amino acid sequence [SEQ. ID. NO: 4] of the N-terminal fragment of HSV-2 gD [Watson, *Gene*, 158:303 (1983)]:

(1) (2) (3) (4) (5) (6) (7) (8) (9)
$NH_2$—Lys—Tyr—Ala—Leu—Ala—Asp—Pro—Ser—Leu—

(10) (11) (12) (13) (14) (15) (16) (17) (18)
Lys—Met—Ala—Asp—Pro—Asn—Arg—Phe—Arg—

(19) (20) (21) (22) (23)
Gly—Lys—Asn—Leu—Pro—COOH

The 23 amino acid sequence [SEQ. ID. NO: 4] of the N-terminal fragment of HSV-1 gD differs from the illustrated sequence of HSV-2 gD in that, in HSV-1 gD, alanine is at position 7 and aspartic acid is at position 21 [Dietzschold et al, *J. of Virol.*, 52(2):431–435 (1984)].

Rather than using the entire 23 amino acid N-terminal protein of HSV-2 gD or HSV-1 gD, certain subunits thereof may be used provided they are capable of inducing a T cell response. A typical subunit of HSV-2 gD is [SEQ. ID. NO: 2]

(8) (9) (10) (11) (12) (13) (14) (15) (16)
—Ser—Leu—Lys—Met—Ala—Asp—Pro—Asn—Arg—

(17) (18) (19) (20) (21) (22) (23)
Phe—Arg—Gly—Lys—Asn—Leu—Pro—

As previously stated, the synthetic peptides corresponding to the above-noted N-terminal fragments may be prepared using the solid phase method described by Merrifield, *Adv. Enzymol.*, 32:221–296 (1969). In a typical coupling reaction, the $^t$Boc group of the amino terminus was removed with 50% trifluoracetic acid (TFA). After neutralization with N,N-diisopropylethylamine (DIEA), a 4- to 6- molar excess of preformed $^t$boc-amino acid-pentafluorophenylester [Kisfaludy et al, *Liebigs Ann. Chem.*, 1421–1429 (1973)] and a 1-molar equivalent of DIEA in dichloromethane (1:1)

were added. After bubbling with $N_2$ gas for 1.5 to 2 hours, the resin was analyzed for the presence of free amino groups as described by [Kaiser et al, *Anal. Biochem.*, 34:595–598 (1970)]. Couplings were repeated until less than 1% free $NH_2$ groups were found.

Other HSV gD fragments which are not immunodominant are also shown to operate according to the method of this invention (see Example 15).

As previously noted, yet another example of a peptide portion of a conjugate employed in a vaccine composition of this invention may comprise a fragment of the nucleoprotein of rabies virus which is an immunodominant T cell antigenic determinant. Other exemplary synthetic rabies peptides which are suitable for use in the present invention are set forth in the following table.

TABLE 1

Synthetic Peptides Corresponding to Antigenic Regions of N and NS

| | | |
|---|---|---|
| 1. Region N-V10 Peptide | | |
| N-V10a: [SEQ ID NO:8] | 383 393 | DDGTVNSDDE |
| N-V10b: [SEQ ID NO:9] | 374 392 | LTKTDVALADDGTVNSDDE |
| N-V10c-L: [SEQ ID NO:10] | 369 383 | $NH_2$—YEAAELTKSDVALAD |
| N-V10c-S: [SEQ ID NO:11] | 369 383 | $NH_2$—YEAAELTKSDVALAD |
| 2. Region N-V12 | | |
| Peptide N-V12a: [SEQ ID NO:11] | 184 203 | $NH_2$—HHTLMTTHKMCANWSTIPNP |
| Peptide N-V12b: [SEQ ID NO:12] | 313 337 | $NH_2$—HFVGCYMGQVRSLNATVIAACAPHE |
| 3. Region NS-V8 | | |
| Peptide NS-V8: [SEQ ID NO:13] | 75 90 | $NH_2$—GKYREDFQMDEGDPS |

A spacer of Gly-Gly-Lys$(NH_2)_2$ may then, preferably, be added to the N-terminus of the peptide fragments. Such addition can be accomplished as part of the synthesis of the N-terminal peptide fragment. Preferably, cysteine is also added at the C-terminus for linkage to other "carrier" molecules, which are generally relatively large proteins.

Saturated fatty acids, generally having from about 11 to about 21 carbon atoms, examples of which are palmitic, stearic and oleic acids, are then coupled to the alpha and epsilon amino groups of the lysine terminus. The procedure by which conjugates of this general type are formed is well known to those of skill in the relevant art [Hopp, *Molecular Immunoloqy*, 21:13–16 (1984)]. As described in Example 16, an experiment was performed in which the fatty acid was varied in the vaccine compositions and methods of the present invention.

Thus prepared, the peptide-fatty acid conjugate is mixed with a liposome composition, which may comprise a mixture of three lipids, namely phosphatidyl choline, cholesterol and lysophosphatidyl choline, according to the method of Thibodeau [Thibodeau et al, "Genetic Variation Among Influenza Viruses", Acad. Press, New York, London, p. 587 (1981)]. The weight proportion of the three constituents of which the liposome is formed may vary considerably. Preferably, the proportion by weight of the three lipids is 16:2:1, respectively.

The peptide-fatty acid conjugate-containing liposome preparation is then mixed with an adjuvant, e.g. alum or complete Freund's adjuvant (CFA). Generally when the adjuvant is CFA a weight ratio of 1:1 is used, resulting in the formation of an emulsion which is available for use in a vaccine. In the case of alum, preferably from about 4 parts to about 16 parts alum by weight, and more preferably about 8 parts by weight alum per part of peptide (in the absence of spacer and fatty acid) may generally be used.

The vaccine is administered in a dosage range of from about 100 to 300 $\mu$g, preferably about 150 $\mu$g, based on the weight of peptide per se (in the absence of spacer and fatty acid), in order to obtain the desired immunogenic T cell response protective against HSV-1 and HSV-2 virus. Usually the vaccine is administered in a single dose and long-term protection against a large infection with herpes virus is provided. However, a series of doses at intervals of several weeks or months followed, if necessary, by a booster dose at an interval of several months to several years may be administered if necessary. So used, the vaccine will produce in laboratory animals a T cell response protective against a herpes virus in the absence of detectable antibody.

Figure 6:
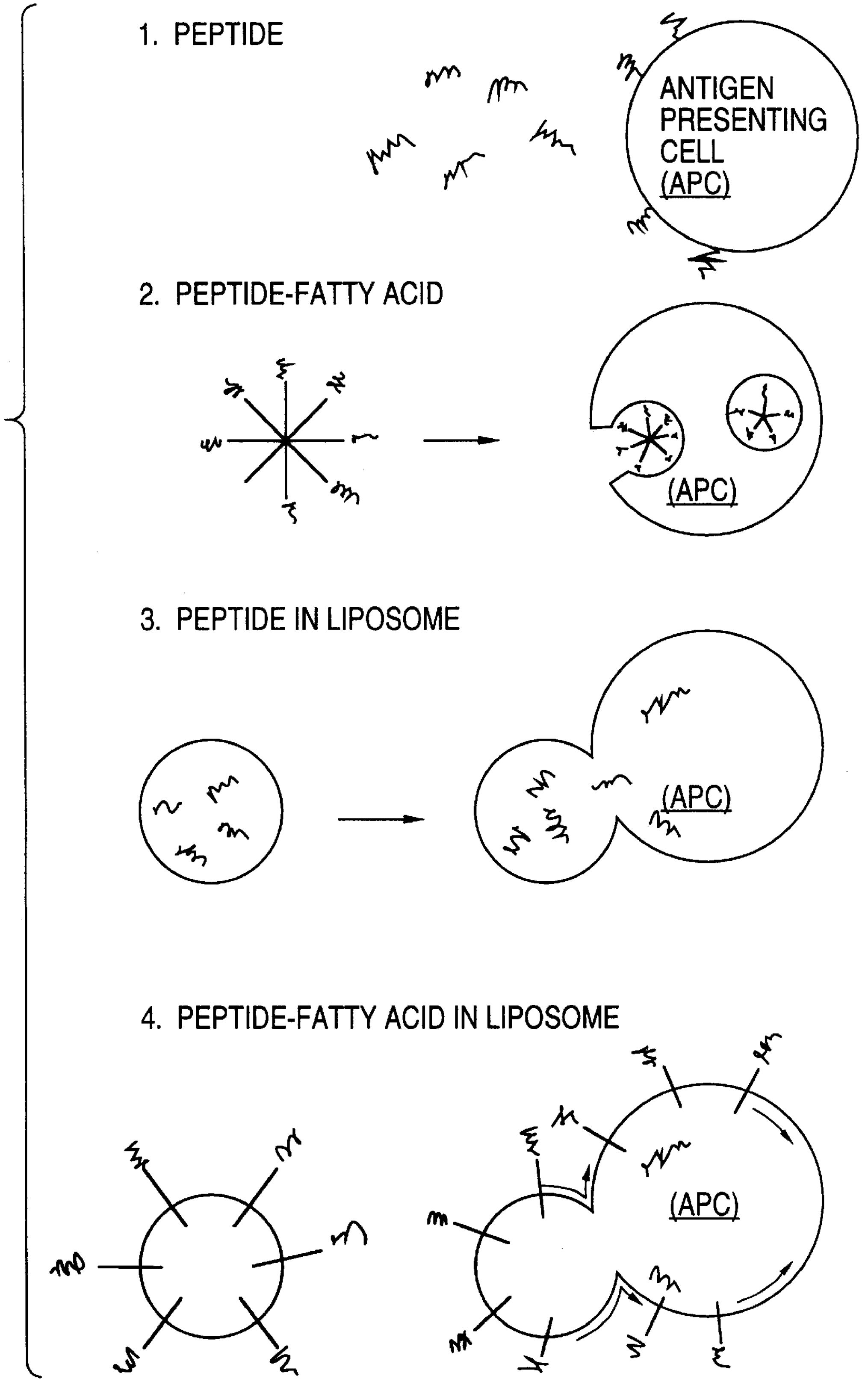
FIG. 6 is a drawing in four sections demonstrating the fusion of a vaccine construct of this invention to the hosts' APC (Section 4) in comparison to three other methods of presenting vaccinal peptides to the hosts' APC (Sections 1 through 3).

The vaccine methods and compositions described in the present invention present the peptide to the APC in a wholly different manner from that of the prior art. T cell protection is elicited by the vaccine methods and compositions of the present invention rather than the antibody protection described by the prior art. FIG. 6 illustrates the mechanisms of exemplary prior art peptide vaccine experiments (Cohen, Hopp and Thibodeau, all cited above) vs. the mechanism of the method of this invention. It is known in the art that B cell responses can be stimulated by the presence of immunogenic peptide sequences. However, cytotoxic, protective T cell immunity is known to require an association of a peptide with an appropriate major histocompatibility complex (MHC) on an APC under certain conditions (See, e.g., M. J. Bevan, *Nature*, 342:479 (1989)].

The inventors submit that it is the manner in which the cited art vaccines present the peptides to the APC which results in their recited observation of B cell protection. Because the present invention presents the peptide to the APC in a wholly different manner, T cell protection is elicited rather than B cell responses.

Section 1 of FIG. 6 demonstrates the presentation of a proposed immunogenic peptide to the APC, such as an HSV peptide described by Cohen, cited above. The peptide itself may survive long enough in the patient's tissue to elicit B cell response, but generally attaches to the surface of the APC in a haphazard fashion and is degraded. Because the peptide is not associated with the APC appropriately, it does not elicit a cytotoxic, protective T cell response.

Section 2 of FIG. 6 demonstrates the Hopp (cited above) vaccine concept, in which peptides are linked to fatty acids, resulting in micelles with hydrophilic regions exposed. Micelles are endocytosed by the APC and dissolve due to the low pH in the cell. It is known that B cells recognize receptors on the surface of micelles. Thus while B cells may respond to the exposed peptides in the micelle prior to endocytosis, no cytotoxic protective T cell immunity is elicited for the same reasons as shown in Section 1.

Section 3 of FIG. 6 demonstrates the vaccine concept of Thibodeau, cited above, which describes entrapping the peptide in a liposome. The liposome adheres and fuses to the APC membrane, and all the contents of the liposome are spilled into the cell. Again the peptides become degraded and dissolved in the APC, resulting in no cellular protection. However, according to Thibodeau, this construct is capable of eliciting B cell responses. There may be enough free peptide in Thibodeau's experiments to account for the B cell production.

The mechanism of the present invention is illustrated in Section 4 of FIG. 6, which shows a new way of associating a peptide with the APC. The peptide-fatty acid conjugate associated with liposome, as described in detail above, forms a structure in which the peptides protrude from the liposome. No micelles are formed. Because the peptides are on the outside of the liposome in the present invention (see FIG. 7, section B), when the liposome-APC membrane fusion occurs, the peptide remains on the cell surface and is permitted to associate with the MHC on the cell surface. The peptide does not degrade inside the cell. The proper association of the peptide with the MHC on the cell surface is what is believed to selectively elicit the cytotoxic protective T cell immunity, in preference to antibody, that is seen in the method of this invention.

Figure 7A:
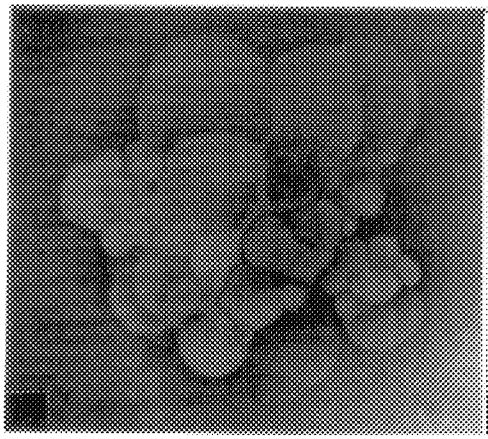
FIG. 7 illustrates two electron micrographs comparing normal liposomes (part A) to the peptide constructs of this invention (part B).
Figure 7B:
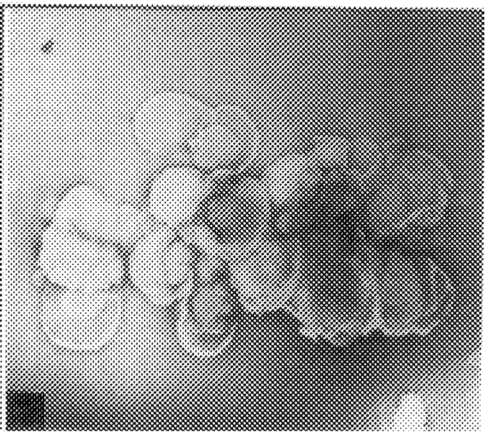

FIG. 7 illustrates an electron micrograph illustrating the difference between a liposome structure on the left side (section A) and a vaccine composition of the present invention (peptide: lipid ratio of 4:1) on the right side (section B). This electron micrograph present evidence that the vaccine compositions of this invention do have a more electron-dense surface with no indication of peptide inside the liposome, and thus provides further evidence of the above-described mechanism of this invention.

The following examples further illustrate specific embodiments of the present invention without, however, limiting the same thereto.

EXAMPLE 1

Pentide Synthesis

A peptide having the sequence homology of the 23 amino acid peptide chain, the sequence of which was deduced from a N-terminal gD molecule of HSV-2, having a spacer of Gly-Gly-Lys added to the N-terminus and cysteine added to the C-terminus, and having the following formula was prepared by Merrifield solid phase methods, cited above.

$(NH_2)_2$Lys—Gly—Gly)*—Lys—Tyr—Ala—Leu— (SEQ ID NO:4)

Ala—Asp—Pro—Ser—Leu—Lys—Met—Ala—Asp—

Pro—Asn—Arg—Phe—Arg—Gly—Lys—Asn—Leu—

Pro—(Cys)**COOH

*A spacer group added to the peptide and to which palmitic acid side chains are added to the Lys amino groups.
**A cysteine amino acid used for linkage to other carrier molecules.

More specifically the peptide molecule having the amino acid sequence immediately above, and sometimes referred to herein as "1-23(2)", was synthesized as follows:

All N-tert-butoxycarbonyl (BOC) amino acids were purchased from Sigma Chemical Co., BOC-Cys-O-Resin, L-t-Amyloxycarbonyl-N-Tosyl-L-Arginine, and L-BOC-O-Benzyl-L-Serine were purchased from Peninsula Laboratories, Inc. Peptides were manually synthesized using Merrifield solid phase methods [Merrifield (1963); Stewart et al (1969) supra] with the following modifications.

A series of three washes, the first with methylene chloride, the second with absolute ethanol and the third with methylene chloride was used instead of dioxane and chloroform before and after deprotection of N-t-BOC amino acid groups. N-t-BOC amino acids were deprotected with 25% trifluoroacetic acid in methylene chloride. Completeness of the deprotection and coupling reactions was monitored using the color tests described by Kaiser et al, *Annal. Biochemistry*, 34:595–598 (1970).

After synthesis the resin was dried, and 50 equivalents of thioanisole were added. The side protection groups were removed and the peptide was cleaved from the resin with anyhydrous hydrogen fluoride. After removal of the anyhydrous hydrogen fluoride, the peptide resin mixture was extensively washed with ethyl acetate and ether to remove the thioanisole. The cleaved peptide was extracted with 1.5% $NH_4CO_3$ and lyophilized. The amino acid sequence of the peptide was verified by automated Edman degradation as described by Hunkapillar and Hood, *Biochemistry*, 17:2124–2133 (1978).

EXAMPLE 2

Synthesis of Fatty Acid-Peptide Conjugate

To add palmitic acid side chains, the N-terminal lysine was coupled as the bis-t-butyloxycarbonyl derivative, then deprotected using trifluoroacetic acid (TFA). The palmitic acid moieties were coupled by the symmetric anhydride method [Hopp (1984) supra]. Thus, the molecule is:

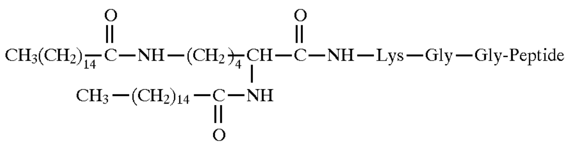

EXAMPLE 3

Synthesis of Vaccine Composition

The fatty acid-peptide conjugate of Example 2 was then mixed with a liposome comprising 3 lipids as follows [see Thibodeau et al (1981), supra]:

Phosphatidyl choline, cholesterol, and lysolecithin were each dissolved in MeOH/chloroform (1:3) and then mixed in the ratio of 16:2:1, respectively. This mixture was then blown down with $N_2$ while rotating the vial in warm $H_2O$ so as to get an even film over the entire vial. Five milligrams of the peptide-palmitic acid conjugate was dissolved in 2 ml of a 1% octylglycoside in phosphate buffered saline solution (PBS). Ten milligrams of the lipid mixture was then added to this peptide solution. Dialysis was carried out against PBS using a 3500 dalton cutoff Spectropore dialysis membrane for 24 hours. The liposomes were sonicated for 5 minutes.

EXAMPLE 4

Testing of the Vaccine

The first experiment performed involved a single injection of the vaccine according to Example 3 (1-23(2) - palmitic acid - liposome in CFA) into the two hind footpads of a group of six Balb/c mice at approximately 150 $\mu$g peptide/animal. The volume given was approximately 0.2 ml/animal or 10 $\mu$g peptide/g body weight.

As controls, Balb/c mice (6 mice/group) were immunized with 1-23(2) peptide palmitic acid in CFA (100 $\mu$g/animal), CFA alone (control), and UV-inactivated HSV-1 in CFA, at 10 PFU/animal.

Six and ½ months after this single immunization, the mice were challenged with a lethal dose (a 10 $LD_{50}$ dose) of HSV-2 strain 186 [Dr. Gary Cohen, University of Pennsylvania] grown in BHK cells in both hind footpads and the animals were examined for the next 30 days for paralysis and death.

The results are plotted in FIG. 1. By day 8, many of the animals were symptomatic. Only two groups, the HSV-1-primed (-◆-◆-) and the 1-23(2) palmitic acid-liposome-CFA-primed (-□-□-) animals, appeared normal. On day 18, when all of the control animals had died [(CFA -◇-◇-); (1-23(2) palmitic acid (-■-■-))], the HSV-1 and 1-23(2)-palmitic acid-liposome-CFA vaccine immunized animals survived. At day 120, 33% of both of those groups were normal.

EXAMPLE 5

Detection of Antibody Response

To determine the mechanism of protection, the antibody response, i.e., the humoral response defined as antibody which can bind the peptide to virus and which can neutralize the activity of virus infectivity in an in vitro assay) was studied. T cells responses were determined by measuring the ability of T cells to respond to antigen by their production of lymphokines after antigen simulation.

Because it is known that neutralizing antibody can protect animals from an HSV infection [Balachandran (1982) supra; Dix et al, *Infect. and Immun.*, 34:192–199 (1981); Kapoor et al, *J. Gen. Virol.*, 60:225–233 (1982)], an effort was made to determine if this was the cause of the protection seen.

Animals were challenged with HSV-2 in the footpads 6 ½ months after a single immunization with antigen in CFA. Animals were bled 1 week after HSV-2 challenge since specific antibody which had already been induced by previous exposure to antigen (peptide) should at that time have been high, and serum was taken from animals and frozen until time of assay. 100 plaque forming units (PFU) of virus in 25 microliters were added to serum antibody in the same volume so that the serum was diluted two fold. This mixture was incubated in 96 well Costar plates for 1 hour at 37° C. BHK cells were then added at a concentration of $5\times10^4$ cells/ml to the 50 microliters. Three to four days later, the cells were stained with crystal violet dissolved in 10% buffer formalin. The results obtained are set forth in Table 2, below.

TABLE 2

Neutralization Titers of Anti-HSV Antibody

| Pooled Serum from Each Group | Neutralizing Antibody for HSV-1 | Neutralizing Antibody for HSV-2 |
|---|---|---|
| 1. Control | 12* | 6 |
| 2. HSV-1 | 389 | 97 |
| 3. 1-23(2) palmitic acid | 6 | 8 |
| 4. Vaccine of Example 3 (1-23(2)palmitic acid-lipsome CFA) | 5 | 5 |

$$\text{*Titer} = \frac{1}{(\text{dilution of sample})2^x} \quad \text{where } x = \text{well number}$$

As shown in Table 2, neutralizing antibody titers may explain the protection observed in the HSV-1 group, but do not explain the protection seen in the group immunized with the vaccine of Example 3 (1-23(2)-palmitic acid liposome CFA).

EXAMPLE 6

Detection of Anti-Viral Binding Activity

Balb/c mice were challenged with HSV-2 in the hind footpads 6 ½ months after a single immunization with the vaccine of Example 3. Bleedings were done 1 week after HSV-2 challenge. A radioimmunoassay was carried out using HSV-1 (-○-○-) and HSV-2 (-Δ-Δ-) infected and uninfected (-■-■-) BHK lysates, and 1-23(H) peptides (-●-●-) and phosphate buffered saline along (-▽-▽-) as immunoadsorbants.

The assay was performed essentially as follows. Vinyl 96-well culture plates containing the five immunoadsorbants identified above were preincubated in saline overnite at 40° C. The plates were then coated with 50% Fetal Calf Serum (FCS). The Balb/c antisera was incubated for 3 hours at room temperature, and $^{125}$I-rabbit Fab anti-mouse Ig was labelled with 5000 counts per minute (CPM).

Figure 2A:
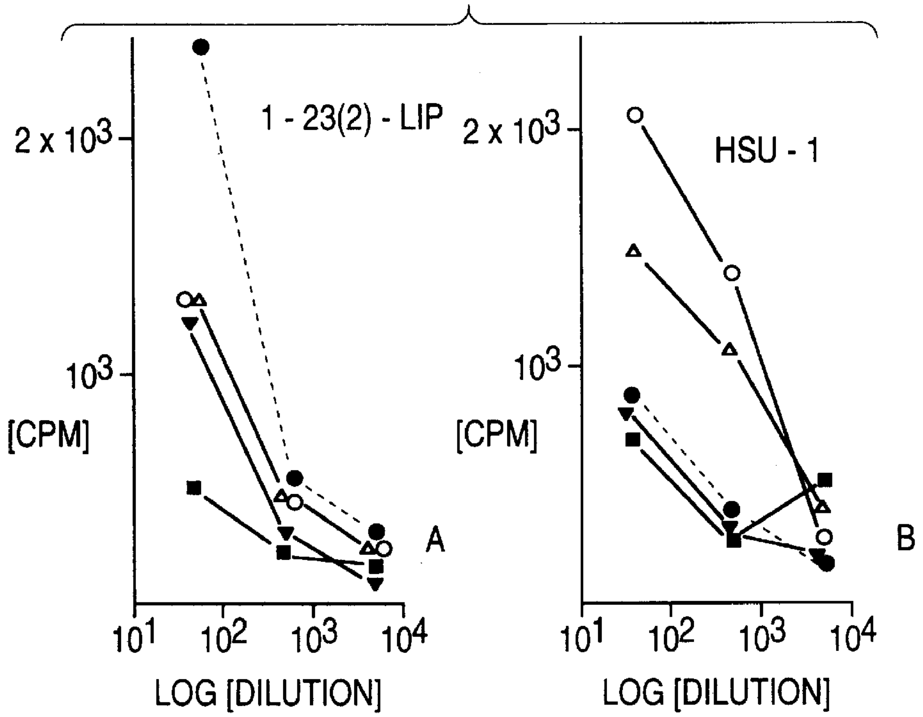
FIGS. 2*a* and 2*b* show the antibody binding activity induced by the HSV vaccine of the invention in relation to certain control inoculants.
Figure 2B:
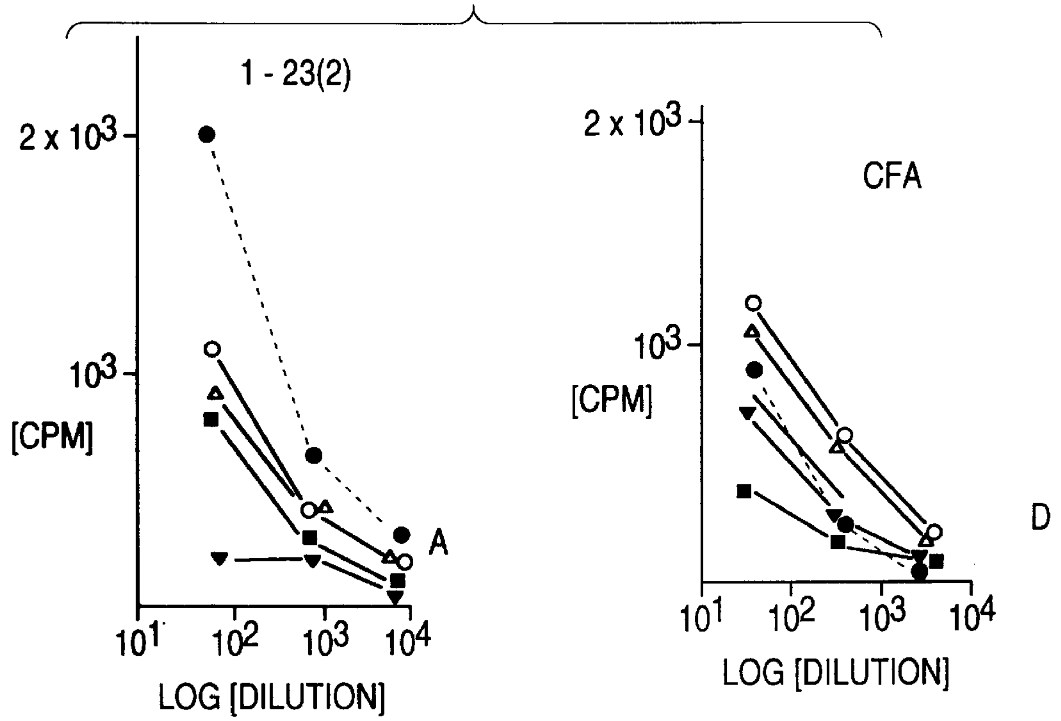

FIGS. 2(*a*) and 2(*b*) plot the amount of radioactively labelled anti-mouse antibody bound against the dilution of the antiserum tested. The following conclusions can be drawn from these results. The highest concentration shown is considered the nonspecific binding region. Anti-peptide binding activity at the highest concentration tested was detected when the animals had been immunized with 1-23 (2) palmitic acid-liposome (A) and 1-23(2) palmitic acid (C), but not with HSV-1 (B) or CFA (D). Although the nature of the binding activity is not clear because it has been detected in the non-specific part of the titration curve, it is clear that antibody to the virus was detected only in animals immunized with HSV-1 (B).

In view of these experiments it has been concluded that the vaccine of the invention induces no detectable antibody which can bind the virus.

EXAMPLE 7

In Vitro T Cell Proliferation Assay

T cells from animals immunized with the vaccine of Example 3 were obtained from the lymph nodes, purified on nylon wool columns [Julius et al, *Europ. J. Immuno.*, 3:645 (1977)], and then tested for responsiveness in vitro for T cell proliferation measured through the incorporation of $^3$H-thymidine into DNA after three days in culture [Corradin et al, *J. Immuno.*, 119:1046 (1977)]. The results appear in Table 3.

TABLE 3

| | |
|---|---|
| T cells alone | 7,300 CPM |
| T cells + 1–23(2) peptide 50 $\mu$g/ml | 30,400 CPM |
| T cells + HSV-1 ($10^6$ PFU/ml) | 20,300 CPM |

The data in Table 3 shows that T cells from animals vaccinated respond to the peptide and also cross-react with the virus. The T cell proliferation test in vitro has generally been accepted as indicative of the presence of an antigen specific T cell response, correlating with T cell effector function. The peptide-containing vaccine of the present invention induces T cells which are responsive not only to the specific peptide but also to a corresponding etiologic agent of the herpes virus infection, i.e. HSV-1.

EXAMPLE 8

Protective Immunity

A further experiment was carried out in the same manner as Example 4. Animals were immunized in the hind footpads with one of the following: (a) 1-23(2)-palmitic acid-liposomes in CFA (13 animals) (-□-□-); (b) UV-inactivated HSV-1 in CFA (5 animals) (-□-□-); (c) CFA alone (10 animals) (-◇-◇-); (d) liposome in CFA (11 animals) (-♦-♦-); and (e) 1-23(2)-palmitic acid-liposome in saline (5 animals) (-■-■-).

Figure 3:
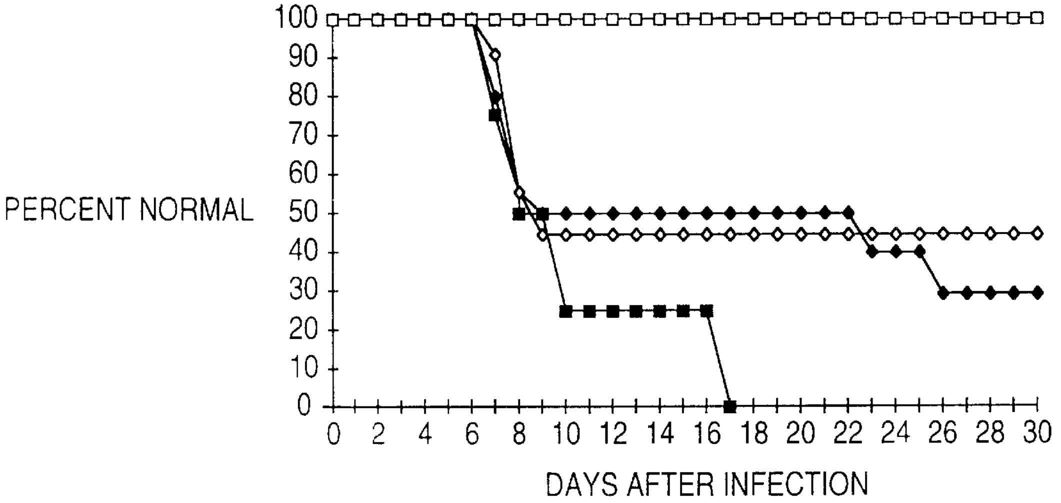
FIG. 3 is similar to FIG. 1, but uses a reduced concentration of herpes virus ($4LD_{50}$ vs. $10LD_{50}$) in the challenge.

The animals were then challenged 3 ½ months after immunization with a 4 $LD_{50}$ of HSV-2 strain 186. The results are presented in FIG. 3. From this figure it can be seen that only the vaccine composition of the present invention and the UV inactivated HSV-1 in CFA protected 100% of the animals from the virus. At least 50% of all animals treated with the other indicated compositions demonstrated virus-caused illness or death.

EXAMPLE 9

Synthesis of Fatty Acid-Peptide Conjugate

The procedures of Examples 1 and 2 were repeated with the exception that the adjuvant used was MDP-Thr, the threnoyl analogue of muramyl dipeptide (N-acetylmuramyl-L-threonyl-D-isoglutamine, a formulation which selectively elicits the formation of antibodies of protective isotypes and of cell mediated immunity [Allison et al, *J. of Immunol. Methods*, 95:157–168 (1986)] was used.

EXAMPLE 10

Testing of the Vaccine

This experiment was performed with a single injection of 1-23(2)-palmitic acid-liposome in CFA vaccine into the two hind footpads of a group of ten Balb/c mice. The volume given was approximately 0.2 ml/animal or 10 μg peptide/g body weight.

Additionally, Balb/c mice (10 mice/group) were immunized with the composition of Example 9 (1-23(2)-palmitic acid-liposome-Thr-MDP as adjuvant) 150 μg peptide/animal or unimmunized as controls.

Figure 4:
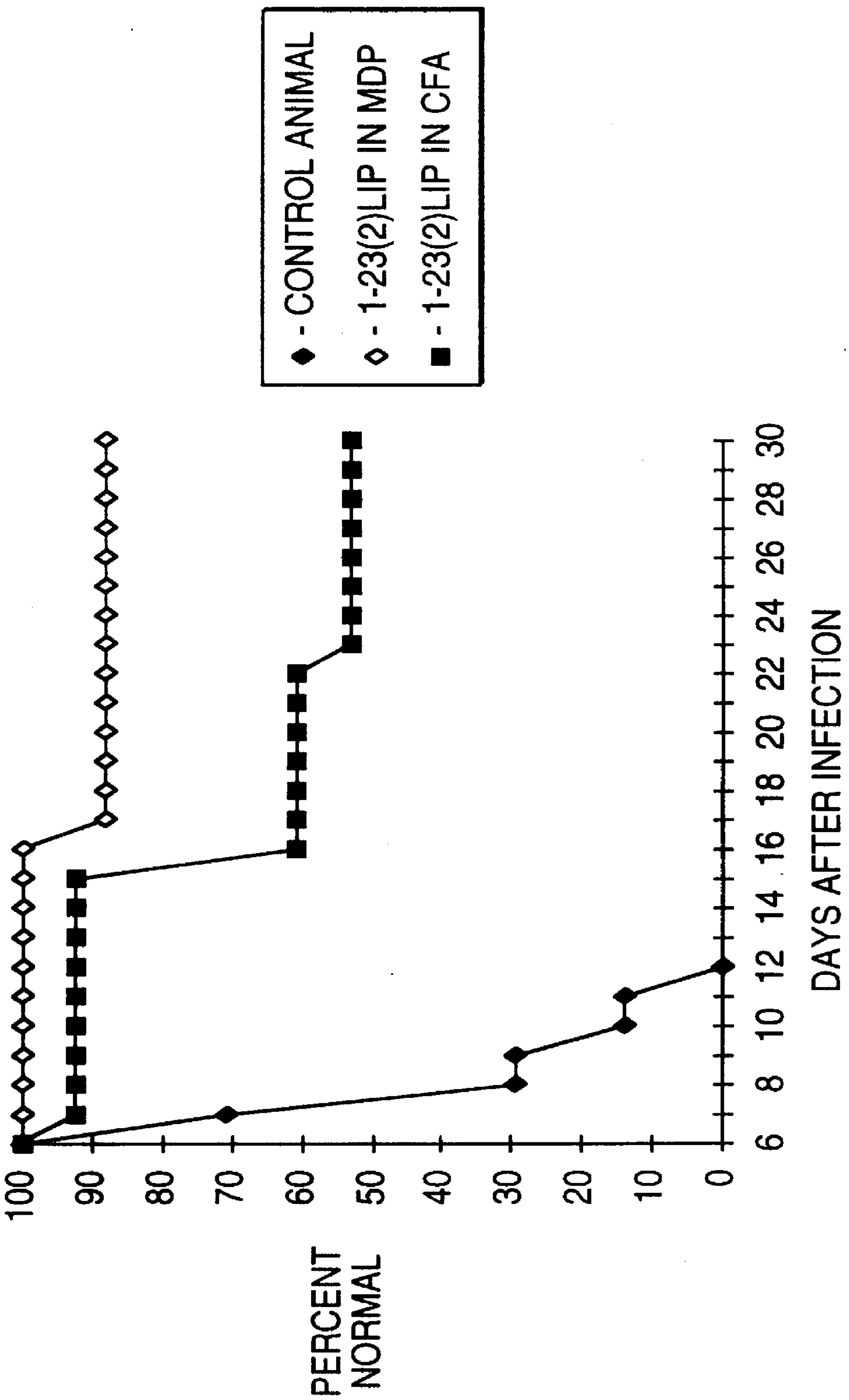
FIG. 4 is a plot of the percentage of normal mice vs. time (days) comparing the protection against lethal infection by HSV-2 provided by a first herpes vaccine of this invention (1-23(2)-liposome in CFA) to a control inoculant and second herpes vaccine of the invention (1-23(2)-liposome in MDP). These two vaccines differ only in the adjuvant used.

Three months after the single immunization, the mice were challenged with a lethal dose of HSV-2 (a 10 $LD_{50}$ dose of strain 186 grown in BHK cells) in both hind footpads and the animals were examined for the next 30 days for paralysis and death. The results are plotted in FIG. 4.

By day 8, many of the animals were symptomatic. Two groups, the 1-23(2) palmitic acid-liposome-Thr-MDP-primed animals (-◇-◇-) and the 1-23(2) palmitic acid-liposome-CFA-primed (-■-■-) animals, appeared normal. On day 15, when all of the control animals had died, almost all of the immunized animals were protected.

EXAMPLE 11

Peptide Synthesis

A peptide having sequence homology to the 25 amino acid peptide chain of rabies nucleoprotein was prepared in a manner analogous to the peptide of Example 1. This peptide had a spacer of Gly-Gly-Lys added to the N-terminus and cysteine added to the C-terminus, and was prepared by Merrifield solid phase methods [Merrifield (1963); Stewart et al (1969), supra]. This peptide has the following formula [SEQ. ID. NO: 5]

$(NH)_2$Lys—Gly—Gly)*

—His—Phe—Val—Gly—Cys—Tyr—Met—Gly—Gln—

Val—Arg—Ser—Leu—Asn—Ala—Thr—Val—Leu—

Ala—Ala—Cys—Ala—Pro—His—Glu—

(Cys)**COOH

*A spacer group added to the peptide and to which palmitic acid side chains are added to the Lys amino groups.
**A cysteine amino acid used for linkage to other carrier molecules.

More specifically, the peptide molecule having the amino acid sequence immediately above, and sometimes referred to herein as "N-V12(b)" [Dietzschold et al, supra], was synthesized as follows:

All N-tert-butoxycarbonyl (BOC) amino acids were purchased from Sigma Chemical Co., BOC-Cys-O-Resin, L-t-Amyloxycarbonyl-N-Tosyl-L-Arginine, and L-BOC-O-Benzyl-L-Serine were purchased from Peninsula Laboratories, Inc. Peptides were manually synthesized using Merrifield solid phase methods [Merrifield (1963); Stewart et al (1969), supra] with the following modifications.

(1) A series of three washes, the first with methylene chloride, the second with absolute ethanol and the third with methylene chloride, was used instead of dioxane and chloroform before and after deprotection of N-t-BOC amino acid groups; (2) N-t-BOC amino acids were deprotected with 25% trifluoroacetic acid in methylene chloride; (3) completeness of the deprotection and coupling reactions was monitored using the color tests described by Kaiser et al, *Annal. Biochemistry*, 34:595–598 (1970). After synthesis the resin was dried, and 50 equivalents of thioanisole were added. The side protection groups were removed and the peptide was cleaved from the resin with anyhydrous hydrogen fluoride. After removal of the anyhydrous hydrogen fluoride, the peptide resin mixture was extensively washed with ethyl acetate and ether to remove the thioanisole. The cleaved peptide was extracted with 1.5% $NH_4CO_3$ and lyophilized. The amino acid sequence of the peptide was verified by automated Edman degradation as described by Hunkapillar and Hood, *Biochemistry*, 17:2124–2133 (1978).

EXAMPLE 12

Synthesis of Fatty Acid Peptide Conjugate

To add palmitic acid side chains, the N-terminal lysine was coupled as the bis-t-butyloxycarbonyl derivative, then deprotected using trifluoroacetic acid. The palmitic acid moieties were coupled by the symmetric anhydride method [Hopp (1984) supra]. Thus, the resulting molecule is:

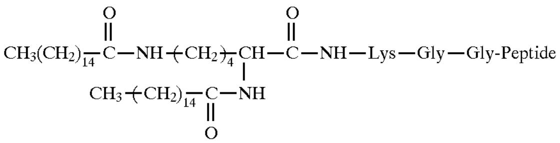

where the peptide fragment is that of N-V12b.

EXAMPLE 13

Vaccine of the Invention

The fatty acid-peptide conjugate of Example 12 was then mixed with a liposome comprising 3 lipids as follows [see Thibodeau et al (1981)]:

Phosphatidyl choline, cholesterol, and lysolecithin were each dissolved in MeOH/chloroform (1:3) and then mixed in the ratio of 16:2:1, respectively. This mixture was then blown down with $N_2$ while rotating the vial in warm $H_2O$ to get an even film over the entire vial. Five mg of the peptide-palmitic acid conjugate was dissolved in 2 ml of a 1% octylglycoside in phosphate buffered saline solution (PBS). Ten milligrams of the lipid mixture was then added to this peptide solution. Dialysis was carried out against PBS using a 3500 dalton cutoff Spectropore dialysis membrane for 24 hours. The liposomes were sonicated for 5 minutes.

EXAMPLE 14

Testing of the Vaccine

The experiment was performed by injecting a single dose of the vaccine of Example 13 (N-V12(b)-palmitic acid-liposome, CFA) into the two hind footpads of a group of eight Balb/c mice. The volume given was approximately 0.2 ml/animal or 10 μg protein/g body weight. In addition, as controls Balb/c mice (10 mice) were immunized with CFA alone.

One month after this single immunization, the mice were challenged with a lethal dose of rabies virus (a 2 $LD_{50}$ dose of strain CVS-24 grown in BHK cells). The animals were examined for the next 21 days for paralysis and death. The results are shown below in Table 4.

TABLE 4

IM Challenge with 2 $LD_{50}$ of CVS-24 4 weeks after immunization

| Vaccine | Mortality* |
|---|---|
| N-V12b-Liposome-CFA | 1/8 |
| None | 7/10 |

The mortality was determined 3 weeks after challenge. As can be seen 87% of the vaccine injected animals survived.

EXAMPLE 15

Challenge Studies of Other Peptides

Six peptides were tested to provide additional examples of peptides in vaccine compositions and methods of the invention described in this application. These peptides are identified by reference to the amino acid numbers of the published HSV gD1 gene sequence of Watson, *Gene*, 26:307–312 (1983). The peptides are identified by number on the bar graph of FIG. 5. Peptide 1 extends from amino acids #1–20 of SEQ. ID. NO: 1; peptide 2 from amino acids #21–40 of SEQ. ID. NO: 1; peptide 3 from amino acids #41–60 of SEQ. ID. NO: 1; peptide 4 from amino acids #61–80 of SEQ. ID. NO: 1; peptide 5 from amino acid #81–100 of SEQ. ID. NO: 1; and peptide 6 from amino acids #101–120 of SEQ. ID. NO: 1.

Each peptide was synthesized by conventional means and prepared as a vaccine composition in combination with palmitic acid and the liposome composition as described for HSV peptide 1-23(2) in detail in Examples 2 and 3 above. Each peptide was tested in a challenge study performed as described in Example 4 above. Briefly, groups of 6 mice were pre-immunized for one month with one of the vaccine compositions containing an indicated peptide, or Complete Freunds Adjuvant (CFA) as a control. The mice were subsequently challenged with HSV2 Strain 186 in the same dosages used in Example 4.

Figure 5:
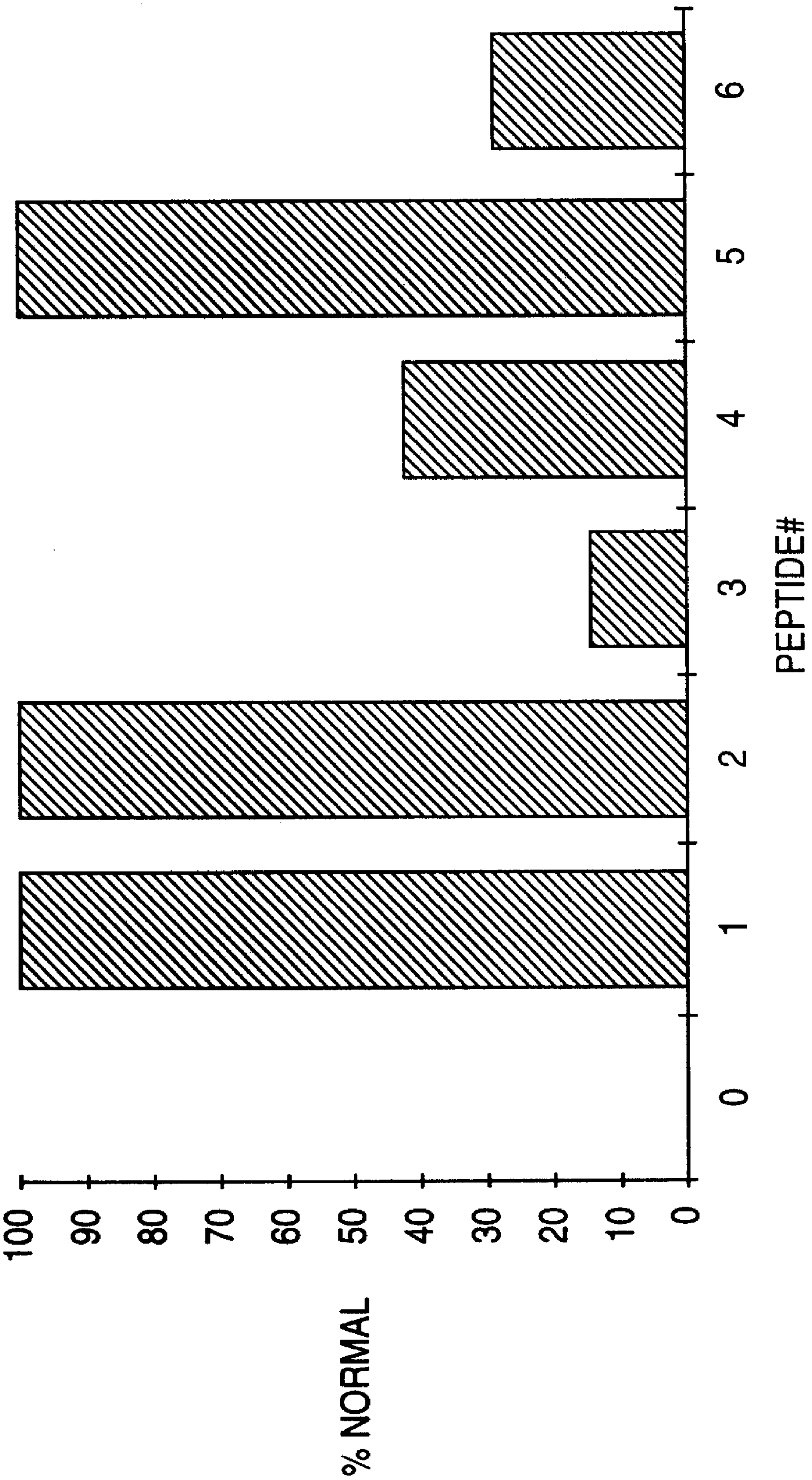
FIG. 5 is a bar graph which demonstrates the effect of six HSV gD1 peptides tested in a challenge study according to the invention and described in Example 15 below.

The animals were determined to be normal (i.e., healthy) or sick, by the same conventional criteria used for the examples in the patent application. Symptoms of unhealthy mice included weight loss, shivering, ruffled fur, paralysis and death. FIG. 5 indicates that all six peptides were capable of producing some degree of protection when administered in the vaccine composition according to the method of this invention. All control (0) animals were sick. Peptides 1, [amino acids #1–20 of SEQ. ID. NO: 1], 2, [amino acids #21–40 of SEQ. ID. NO: 1] and 5 [amino acids #81–100 of SEQ. ID. NO: 1] completely protected 100% of the animals. Peptides 3, [amino acids #41–60 of SEQ. ID. NO: 1], 4, [amino acids #61–80 of SEQ. ID. NO: 1] and 6 [amino acids #101–120 of SEQ. ID. NO: 1] completely protected 15%, 40% and 28% of the animals, respectively.

These results illustrate that the immunodominance of the peptide used in the vaccine compositions and methods of this invention is irrelevant to the issue of whether the vaccine is capable of exerting a protective effect. The efficacy of the methods of this invention lies in the manner in which the conjugate presents the peptide to the host's APCs. The precise identity of the peptides capable of inducing a T cell response, which are used in the vaccine compositions and methods, is not critical and should not be limited to these or other illustrative peptides.

EXAMPLE 16

Vaccine Formulations

Vaccine compositions were prepared according to the procedures described in Examples 2 and 3 above using peptide HSV 1-23(2), the sole change being the fatty acid used. One vaccine composition employed myristic acid in place of palmitic acid. Another vaccine composition employed stearic acid in place of palmitic acid. Liposome without fatty acid was used as the control. Each vaccine composition was then employed in a vaccine test performed as described in Example 4.

When the animals were examined on days 8, 9, and 10 after viral challenge, the percentage of healthy animals was determined as described above for the previous test. The results are shown in Table 5 below. Palmitic acid provided the best results, protecting 80 to 100% of the animals in the test group. However, both myristic acid (up to 60% protected) and stearic acid (from 20 to 60% protected for some duration) in the vaccine compositions of this invention also demonstrated some ability to protect animals from the virus.

TABLE 5

Protection of Mice from HSV with Peptide-Lipid Conjugates Incorporated into Liposomes

| | Days after HSV-2 Challenge | | |
|---|---|---|---|
| | 8 | 9 | 10 |
| Palmitic Acid | 100* | 100 | 80 |
| Myristic Acid | 60 | 60 | 60 |
| Stearic Acid | 60 | 40 | 20 |
| Liposome Control | 40 | 20 | 20 |

*% of animals without symptoms

The published articles identified in the foregoing specification are incorporated by reference herein in their entirety.

We claim:

1. A method for inducing a cylotoxic T cell response in a mammalian host against a viral infection comprising administering to the host an immunologically effective amount of a peptide-fatty acid conjugate of the formula:

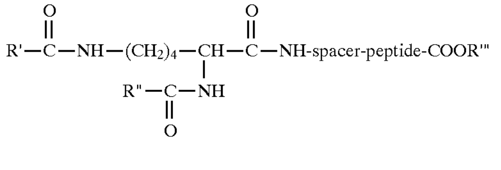

where R' and R" are alkyl groups containing from 5 to 30 carbon atoms, and R"' is selected from the group consisting of hydrogen and at least one amino acid residue; wherein the peptide comprises an amino acid sequence corresponding to the sequence of a fragment of a viral protein which fragment produces a protective T cell response; and wherein the peptide-fatty acid conjugate is administered in association with a liposome composition and an adjuvant so that the peptide protrudes from the liposome.

2. The method according to claim 1 wherein said spacer is a peptide having the sequence -Lys-Gly-Gly-.

3. The method according to claim 1 in which the adjuvant is selected from the group consisting of alum, complete Freund's adjuvant, and N-acetylmuramyl-L-Threonyl-D-isoglutamine (MDP-Thr).

4. The method according to claim 1 in which each of R' and R" is an alkyl group containing from 10 to 20 carbon atoms.

5. The method according to claim 1 in which each R' and R" is an alkyl group containing 15 carbon atoms, and R"' is a cysteine residue, and the adjuvant is alum.

6. The method according to claim 1 in which said liposome composition comprises a mixture of phosphatidyl choline, cholesterol and lysophosphatidyl choline.

7. The method according to claim 6 in which said phosphatidyl choline, cholesterol and lysophosphatidyl choline are present in the proportions by weight of 16:2:1, respectively.

8. The method according to claim 1 which further comprises administering to said host said conjugate in an amount that provides from about 100 to about 300 μg by weight of said peptide per dose.

9. A method for inducing a cytotoxic T cell response in a mammalian host against a Herpes Simplex Virus Type I or Type II viral infection comprising administering to the host an immunologically effective amount of a peptide-fatty acid conjugate of the formula:

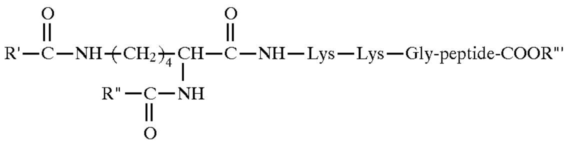

wherein R' and R" are alkyl groups containing from 5 to 30 carbon atoms, and R"' is selected from the group consisting of hydrogen and at least one amino acid residue;

wherein said peptide is selected from the group consisting of (a) -Ser-Leu-Lys-Met-Ala-Asp-Pro-Asn-Arg-Phe-Arg-Gly-Lys-(Asn or Asp)-Leu-Pro- SEQ ID NO:6; and (b) -Lys-Tyr-Ala-Leu-Ala-Asp-(Pro or Ala)-Ser-Leu-Lys-Met-Ala-Asp-Pro-Asn-Arg-Phe-Arg-Gly-Lys-(Asn or Asp)-Leu-Pro- SEQ ID NO:7;

in association with a liposome composition and adjuvant, wherein the peptide protrudes from the liposome.

10. The method according to claim 9 wherein R' and R" are each $CH_3(CH_2)14$-, R"' is H, and said liposome comprises a mixture of phosphatidyl choline, cholesterol and lysolecithin in proportions by weight of 16:2:1.

11. A vaccine composition against Herpes Simplex Virus Type I or Type II comprising a peptide-fatty acid conjugate having the formula:

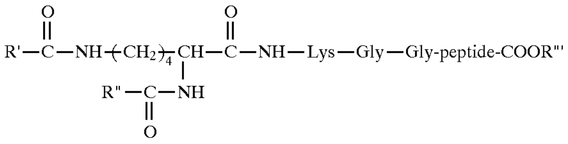

wherein R' and R" are alkyl groups containing from 5 to 30 carbon atoms, and R"' is selected from the group consisting of hydrogen and at least one amino acid residue;

wherein said peptide is selected from the group consisting of (a) -Ser-Leu-Lys-Met-Ala-Asp-Pro-Asn-Arg-Phe-Arg-Gly-Lys-(Asn or Asp)-Leu-Pro- SEQ ID NO:6; and (b) -Lys-Tyr-Ala-Leu-Ala-Asp-(Pro or Ala)-Ser-Leu-Lys-Met-Ala-Asp-Pro-Asn-Arg-Phe-Arg-Gly-Lys-(Asn or Asp)-Leu-Pro- SEQ ID NO:7;

in association with a liposome composition and adjuvant, wherein the peptide protrudes from the liposome and induces a protective T cell response in said host.

12. The composition according to claim 11 wherein R' and R" are each $CH_3(CH_2)14$-, R"' is H, and said liposome comprises a mixture of phosphatidyl choline, cholesterol and lysolecithin in proportions by weight of 16:2:1.

13. The method according to claim 1 in which the viral protein is a glycoprotein.

14. The method according to claim 1 in which the peptide is a synthetic peptide.

15. The method according to claim 1 wherein said viral infection is herpes simplex virus type 1.

16. The method according to claim 15 wherein said peptide is a fragment of herpes simplex virus type 1 envelope glycoprotein gD-1.

17. The method according to claim 1 wherein said viral infection is herpes simplex virus type 2.

18. The method according to claim 17 wherein said peptide is a fragment of herpes simplex virus type 2 envelope glycoprotein gD-2.

19. The method according to claim 1 wherein said viral infection is rabies virus.

20. The method according to claim 19 wherein said peptide is a fragment derived from the nucleoprotein of said rabies virus.

21. The method according to claim 20 wherein said peptide is

—His—Phe—Val—Gly—Cys—Tyr—Met—

Gly—Gln—Val—Arg—Ser—Leu—Asn—

Ala—Thr—Val—Ile—Ala—Ala—Cys—

Ala—Pro—His—Glu— of SEQ ID NO: 3.

of SEQ ID NO: 3.

* * * * *